United States Patent [19]
Kimura et al.

[11] Patent Number: 5,896,804
[45] Date of Patent: Apr. 27, 1999

[54] SYRINGE PUMP

[75] Inventors: Rokusaburo Kimura; Nobuhiro Kitagawa, both of Kobe, Japan

[73] Assignee: Toa Medical Electronics Co., Ltd., Hyogo, Japan

[21] Appl. No.: 08/959,926

[22] Filed: Oct. 29, 1997

[30] Foreign Application Priority Data

Oct. 29, 1996 [JP] Japan .................................. 8-286797
Oct. 3, 1997 [JP] Japan .................................. 9-271649

[51] Int. Cl.$^6$ ........................................................ B67D 5/08
[52] U.S. Cl. ................................................ 92/31; 92/136
[58] Field of Search ............................... 92/136, 31, 54

[56] References Cited

U.S. PATENT DOCUMENTS

| | | | |
|---|---|---|---|
| 2,936,737 | 5/1960 | Miller | 92/31 |
| 3,411,409 | 11/1968 | Bunyard | 92/136 |
| 3,771,918 | 11/1973 | Winter | 92/136 |
| 4,475,666 | 10/1984 | Bilbrey et al. | 422/922 |

*Primary Examiner*—Sheldon J. Richter

[57] ABSTRACT

A compact syringe pump having a high quantitative accuracy and a high durability is provided. The syringe pump comprises a motor, a rotating cylinder, a moving element, a guide means for introducing the moving element in an axial direction of the rotating cylinder, a piston rod disposed on the moving element and a cylinder within which the piston rod moves, wherein the guide means comprises a guide pin extending through the moving element in the axial direction of the rotating cylinder and a pair of upper supporting member and lower supporting member for supporting both ends of the guide pin so that the guide pin becomes in parallel to the axial direction of the rotating cylinder, the upper supporting member rotatably supports the rotating cylinder at an upper end portion of the rotating cylinder and the lower supporting member rotatably supports the rotating cylinder at an upper surface portion of the bottom portion of the rotating cylinder, thereby preventing the rotating cylinder from swinging.

5 Claims, 6 Drawing Sheets

SYRINGE PUMP

BACKGROUND OF THE INVENTION

1. Field of the Invention:

The present invention relates to a syringe pump for sucking and discharging a fluid, which is used for an automatic analyzing apparatus.

2. Description of the Related Art:

Conventionally, there is a syringe pump for sucking and discharging a fluid, which comprises a lead screw connected to a rotational shaft of a motor, a moving element screwed to the lead screw, a piston mounted to the moving element and a cylinder in which the piston slides. Generally, since the lead screw in a driving side and the piston in a load side have parallel axes to each other, the load from the piston uniformly acts on the driving side so that there is problems in a quantitative accuracy and a durability, for example, engagement between the lead screw and the moving element lacks smoothness, rotation of the motor lacks in uniformity and the like.

Then, as disclosed in U.S. Pat. No. 4,475,666, an apparatus in which the axes of the driving side and the load side are linearly disposed on a line so as to coincide the axis of the drive side with the axis of the load side has been considered. The apparatus comprises a sleeve 29 having a threaded portion in an inner peripheral portion, a nut 25 engaged with an inside of the sleeve 29, a piston 16 provided in a center of the nut 25 and movable within an inner portion of a cylinder 15 and a motor 33 for rotating the sleeve 29 through a belt 32 meshed with an outer peripheral lower portion of the sleeve 29, in which the motor 33 is disposed side by side with the sleeve 29. Further, two brackets 34 extends through the inside of the sleeve 29 from an upper portion of the sleeve 29 and are fastened to each other in a lower portion of the sleeve 29 by a plate 36 so that when the sleeve 29 is rotated, the brackets 34 restrict the rotation of the nut 25 and act as a rotation preventing means for introducing the nut 25 in an axial direction of the sleeve 29. The outer peripheral lower portion of the sleeve 29 is supported by a radial ball bearing 30.

In the above syringe pump, since the motor 33 and the sleeve 29 are disposed side by side in a lateral direction although the axis of the piston 16 and the axis of the sleeve 29 are disposed on a line, the apparatus is totally widened toward the lateral direction, thereby preventing a miniaturization. Accordingly, it can be considered that the motor 33 is disposed immediately below the sleeve 29 so as to directly rotate the sleeve 29, however, since the bracket 34 extends through the sleeve 29 in a vertical direction, it is difficult to rotatably hold the sleeve 29.

On the contrast, since the sleeve 29 is pivotally supported in the lower portion of the body thereof, the sleeve 29 is easily swung in a radial direction and an axial direction, particularly, the upper portion thereof is swung in a radial direction so that a straight drivability of the piston 16 is hardly secured, thereby generating problems in view of the quantitative accuracy and the durability.

SUMMARY OF THE INVENTION

An object of the present invention is to provide a compact syringe pump having a high quantitative accuracy and a high durability.

In accordance with the present invention, there is provided a syringe pump comprising: a driving means having a rotating shaft; a rotating cylinder having a bottom, a connecting portion capable of connecting with the driving means at a lower surface of the bottom and a threaded portion formed in an inner peripheral portion; a moving element having in an outer peripheral portion; a threaded portion to engage with the threaded portion of the rotating cylinder; a guide means for introducing the moving element in an axial direction of the rotating cylinder by restricting the rotation of the moving element when the rotating cylinder rotates through the connecting portion; a syringe piston disposed on the moving element; and a syringe cylinder within which the syringe piston moves, wherein the guide means comprises a guide pin extending through the moving element in the axial direction of the rotating cylinder and a pair of upper supporting member and lower supporting member for supporting both ends of the guide pin so that the guide pin becomes in parallel to the axial direction of the rotating cylinder, and the supporting members are structured such that the upper supporting member rotatably supports the rotating cylinder at an upper end portion of the rotating cylinder and the lower supporting member rotatably supports the rotating cylinder at an upper surface of the bottom of the rotating cylinder.

DETAILED DESCRIPTION OF THE PREFERRED EMBODIMENT

Figure 1:
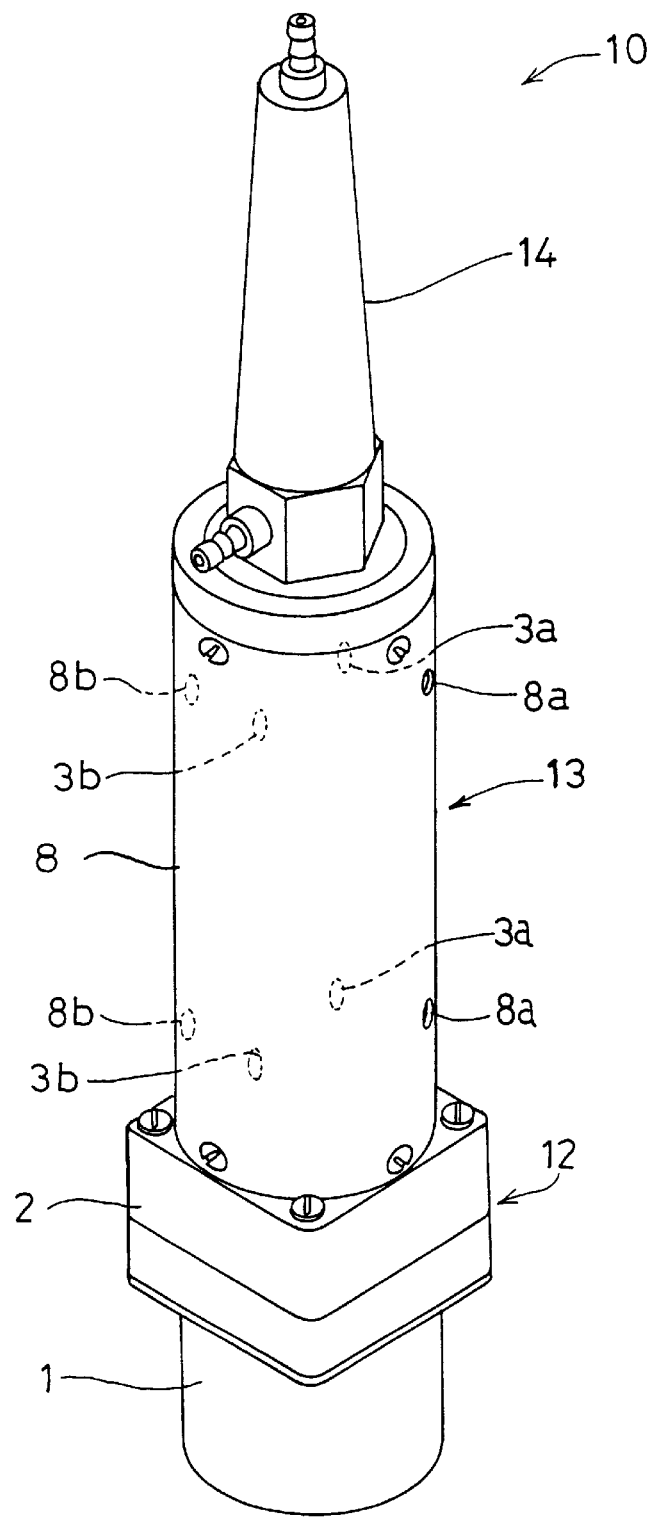
FIG. 1 is a schematic view which wholly shows a syringe pump in accordance with an embodiment of the present invention.

The syringe pump in accordance with the present invention may be a pump in which the piston is intermittently ascended and descended within the cylinder by rotating the motor in both normal and reverse directions, or may be a reciprocating pump which reciprocates the piston within the cylinder by rotating the motor in one direction.

It is preferable that the driving means in accordance with the present invention is a servo motor or a pulse motor in which the rotating axis thereof can be rotated at a predetermined rate.

It is preferable that the moving element in accordance with the present invention is a disc which can move along the axial direction of the rotating cylinder for a predetermined distance in an engaging state with the threaded portion of the rotating cylinder.

It is preferable that the guide means in accordance with the present invention serves as a linear conversion mechanism which introduces the moving element toward the axial direction of the rotating cylinder by preventing the moving element engaged with the rotating cylinder from rotating together with the rotating cylinder when the rotating cylinder rotates.

In accordance with the present invention, one or a plurality of syringe piston(s) may be mounted on the moving element. The syringe pistons are placed in good balanced positions on a surface of the moving element which is perpendicular to the axis so that the surface of the moving element is not inclined when the moving element receives a load from the syringe pistons. The moving direction of the moving element is thus kept in parallel with the axis.

It is preferable that the syringe piston is placed at the center of the moving element in the case where only one syringe piston is mounted. In the case where a plurality of syringe pistons are mounted, it is preferable that the syringe pistons are dispersed symmetrically around the center of the moving element. In other words, it is preferable that the syringe pistons are spaced equidistantly from the center of the moving element.

It is preferable that the guide pin in accordance with the present invention is freely fitted to the hole extending through the moving element in a state of having a sufficient gap to smoothly slide with respect to the hole.

The supporting member in accordance with the present invention is a bearing for the rotating cylinder and pivotally supports the rotating cylinder by a sliding contact and a rolling contact, and preferably a thrust bearing, a radial bearing or a conical bearing using a bush or a bearing. More preferably, it is preferable that an annular holding portion is formed on each of opposing portions thereof, thereby producing a rolling contact by a plurality of rolling members inserted therebetween. The holding portion comprises, for example, a perpendicular groove in which two track surfaces in thrust and radial directions perpendicularly cross.

It is desirable that the upper and lower supporting members are fastened to each other by the guide pin in a vertical direction.

It is preferable that the guide pin comprises a plurality of guide pins between the upper supporting member and the lower supporting member.

In the syringe pump in accordance with the present invention, when the rotating axis is normally rotated by the driving means, the rotating force is transmitted from the driving means to the rotating cylinder through the connecting portion. When the rotating cylinder is rotated, the moving element engaged with the threaded portion of the rotating cylinder tends to rotate together with the rotating cylinder, however, the guide shaft both ends of which are fixed by the supporting member serves as a rotation preventing means for the moving element, thereby moving the moving element along the threaded portion of the rotating cylinder in the axial direction. The piston fixedly attached to the moving element reciprocates so as to give pressure and motion to a liquid within the cylinder.

Since the upper supporting member pivotally supports the rotating cylinder at the upper end portion of the rotating cylinder in such a manner as to rotate, the swing in a radial direction and an axial direction in the upper portion of the rotating cylinder can be prevented. Further, since the lower supporting member pivotally supports the rotating cylinder at the upper surface portion of the bottom portion of the rotating cylinder in such a manner as to rotate, the swing in the lower portion of the rotating cylinder can be prevented. Since the guide pin is supported by the upper and lower supporting members at both ends thereof, the guide axis effectively operates as the rotation preventing mechanism for the moving element. Further, if the upper and lower supporting members are vertically fastened to each other by the guide pin, the guide pin and the supporting members integrally improve the rigidity, the distortion of the attitude of the guide pin can be prevented and the upper and lower supporting members in a cooperating manner support an upper and lower two portions of the rotating cylinder so that the total swing of the rotating cylinder in the radial direction and the axial direction can be effectively prevented.

If the plurality of guide pins are provided between the upper supporting member and the lower supporting member, when the rotating cylinder is going to rotate, the force obtained by that the moving element engaged with the rotating cylinder is going to rotate together with the rotating cylinder can be dispersed into the plurality of guide pins. Accordingly, the distortion of the attitude of the guide pin in the radial direction can be prevented. Further, the upper supporting member and the lower supporting member can be easily maintained in parallel. By mounting a plurality of the syringe pistons dispersedly on the moving element and providing the syringe cylinders for the individual syringe pistons, it becomes possible to operate a plurality of fluid systems with one driving source.

Figure 2:
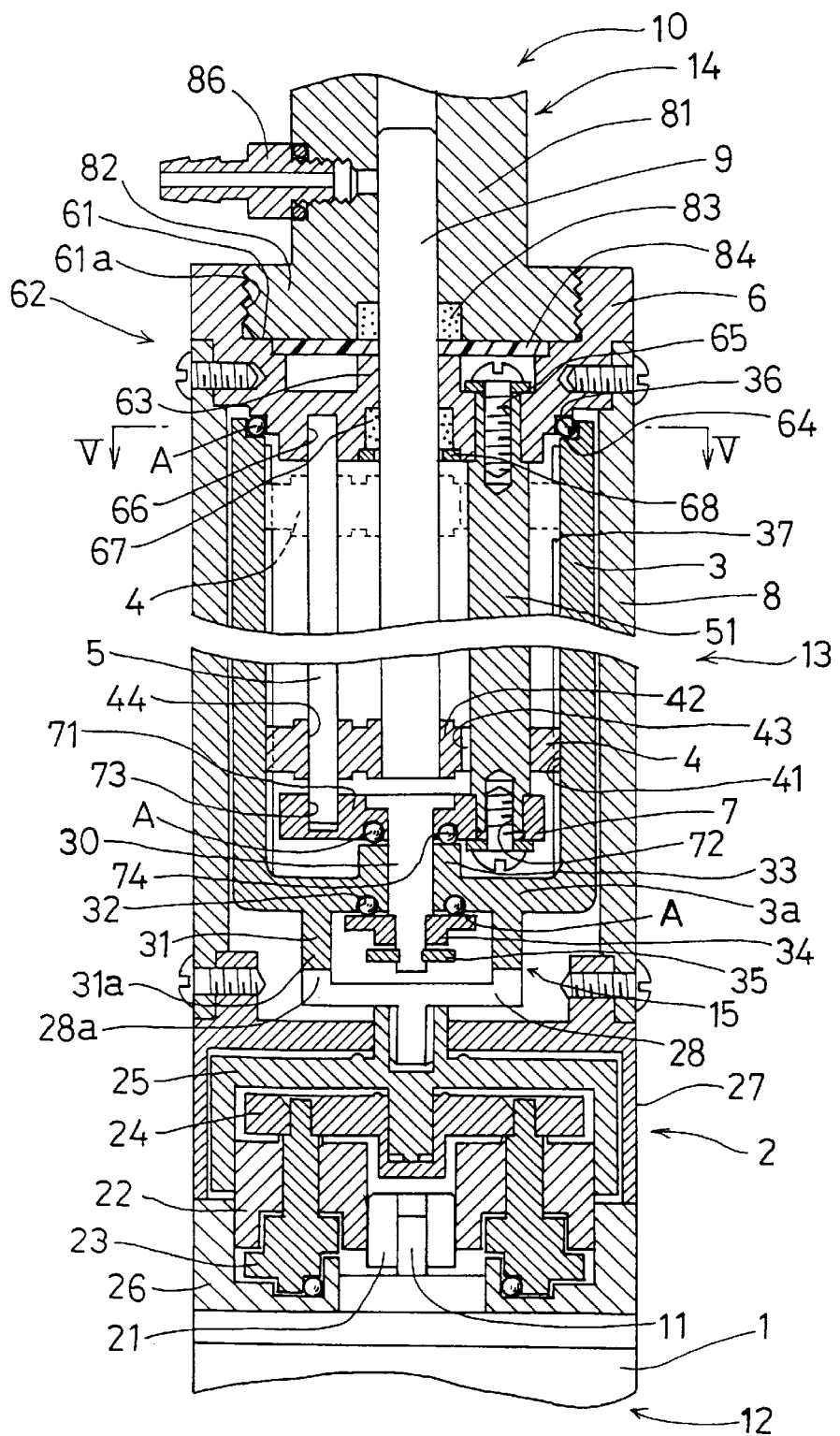
FIG. 2 is a cross sectional view which shows a main part of the syringe pump shown in FIG. 1.

FIGS. 1 and 2 show a syringe pump in accordance with an embodiment of the present invention. A syringe pump 10 is provided with a driving member 12 having a rotating shaft 11, a linear converting portion 13 and a syringe member 14 on the same axis.

Figure 3:
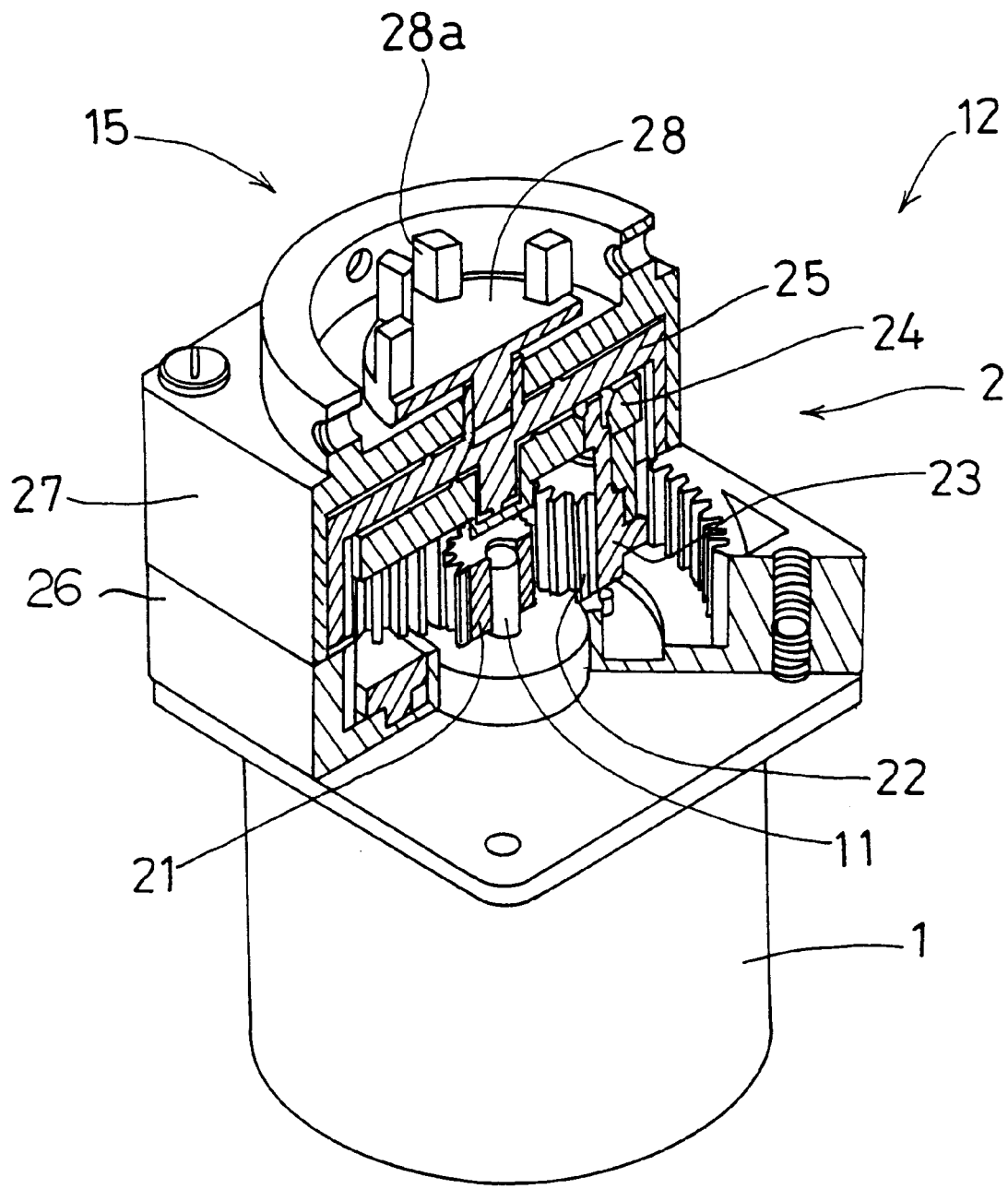
FIG. 3 is a perspective view which partially shows a cross section of a driving portion and a connecting portion of the syringe pump shown in FIG. 1.

As shown in FIGS. 2 and 3, the driving member 12 comprises a stepping motor 1 and a reduction gear 2 connected to each other. The reduction gear 2 has a rotational force transmitting system comprising a planetary gear 22 driven through a pinion 21 fixedly attached to the rotating shaft 11 of the stepping motor 1 and a motor mounting base 26, a planetary gear base 23, a planetary gear base holder 24 and a movable internal gear 25, and these elements are mounted to an upper portion of the stepping motor 1 by the motor mounting base 26 and a cover 27. A connecting portion 15 is formed above the reduction gear.

The connecting portion 15 comprises a disc like lower coupling 28 fixedly attached to the central axis of the movable internal gear 25 and an annular upper coupling 31 formed on a lower surface of a bottom portion 3a of a rotating cylinder 3 mentioned below. The lower coupling 28 is provided with a lower projection 28a projecting from an upper surface thereof upwardly at a substantially equal interval, which can engage with an upper projection 31a projecting from the upper coupling 31 thereof downward at a substantially equal interval. The cover 27 is connected to the linear converting portion 13 at an upper portion thereof.

Figure 4:
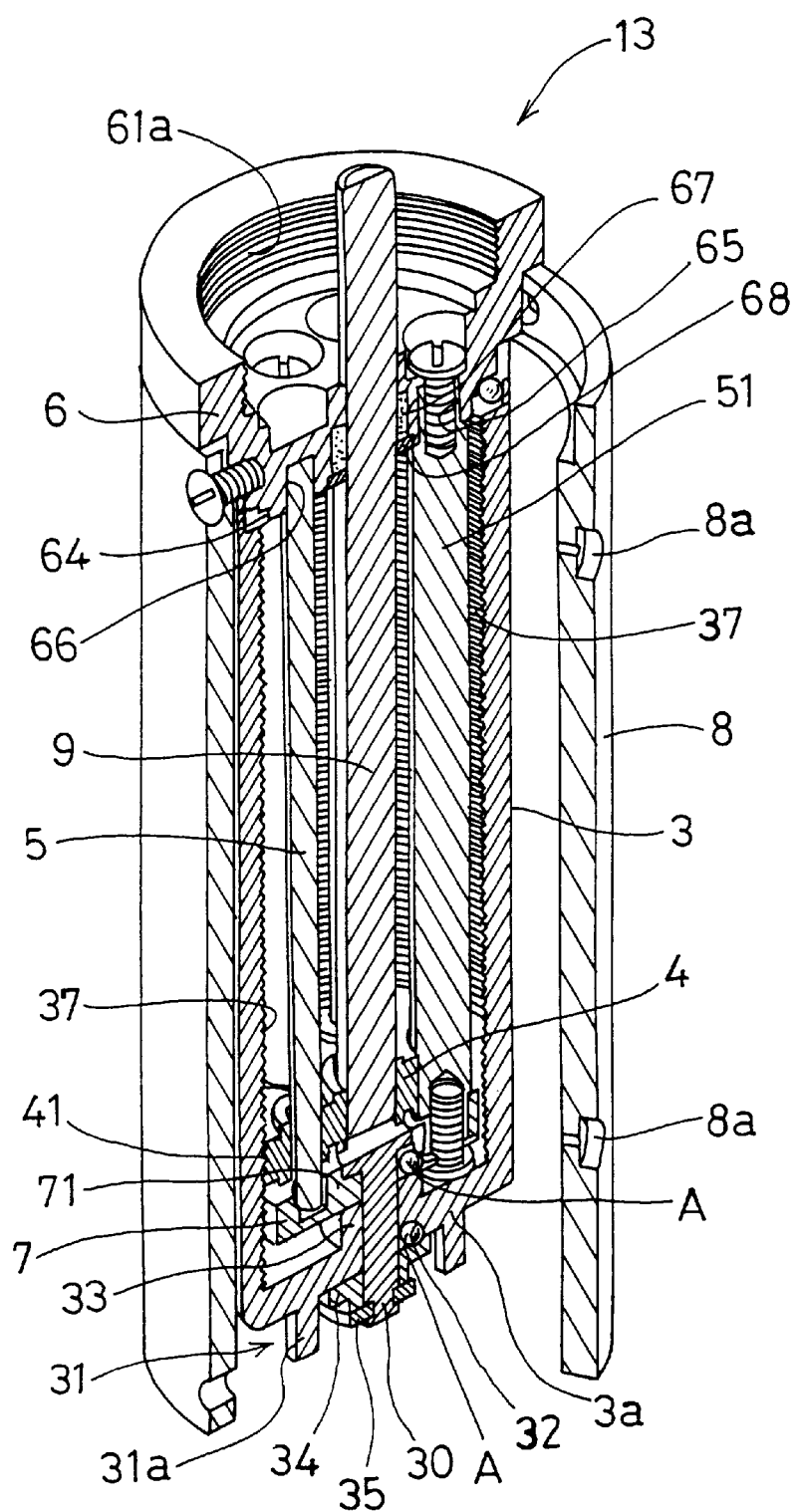
FIG. 4 is a perspective view which partially shows a cross section of a linear converting portion of the syringe pump shown in FIG. 1.

The linear converting portion 13 comprises, as shown in FIG. 4, the rotating cylinder 3, a moving element 4, a guide pin 5, an upper supporting member 6, a lower supporting member 7 and an outer cylinder 8. The rotating cylinder 3 is an axially symmetrical metal cylinder having the bottom portion 3a and is provided with a boss 33 of a supporting shaft 30 pivotally supporting the lower supporting member 7 mentioned below in such a manner as to rotate on the upper surface of the rotating cylinder 3 in a center of the bottom portion 3a. The supporting shaft 30 extending through the boss 33 is supported by a thrust collar 34 and a snap ring 35 at a lower portion thereof. The thrust collar 34 pivotally supports the rotating cylinder 3 by a rolling contact due to a ball A inserted into an annular holding portion 32 provided on the lower surface of the bottom portion 3a.

A holding portion 36 is formed on an opening end surface of the upper portion of the rotating cylinder 3 (refer to FIG. 2). The holding portion 36 is formed with a perpendicular groove comprising horizontal and vertical planes perpendicularly crossing to each other in the inner peripheral portion of the above end surface all around the periphery.

The inner peripheral portion of the rotating cylinder 3 is provided with a parallel threaded portion (a female screw) 37 substantially all around the surface, and the threaded portion 37 is provided with the moving element 4 in which a threaded portion (a male screw) 41 engaged with the threaded portion 37 at the outer peripheral portion thereof.

The moving element 4 is made of metal disc, and a lower end of a piston rod 9 mentioned below is fixed to a boss 42 formed in a center thereof in such a manner as not to rotate. A large and small through holes 43 and 44 are formed between the boss 42 and the threaded portion 41 on a substantially concentric circle at an equal interval, and a supporting column 51 and the guide pin 5 are respectively inserted into the through hole 43 having a large diameter and the through hole 44 having a small diameter. The piston 9 has an axis extending in a coinciding manner with the axis of the rotating cylinder 3, and both ends of the support column 51 and the guide pin 5 are respectively supported by the upper supporting member 6 and the lower supporting member 7 in such a manner that the respective axes are parallel to the piston rod 9.

Figure 5:
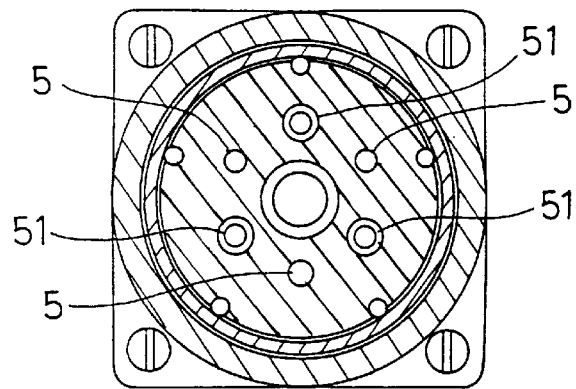
FIG. 5 is a cross sectional view along a line V—V in FIG. 2.

The upper supporting member 6 can receive the base portion of the syringe member 14, is a metal disc comprising a recess portion 61 opened upward, a supporting portion 62 supporting the upper end of the rotating cylinder 3 and a boss 63 through which the piston rod 9 extends, and a threaded portion 61a is formed on the inner peripheral surface of the recess portion 61. A holding portion 64 for the ball A is formed on the lower surface of the supporting portion 62. FIG. 5 is a cross section taken on line V—V in FIG. 2.

The holding portion 64 is formed with a perpendicular groove comprising horizontal and vertical planes perpendicularly crossing to each other at the outer peripheral portion of the above lower surface all around the periphery thereof. Fixing holes 65 and 66 fixing the respective upper end of the support column 51 and the guide pin 5 in such a manner as not to rotate, as shown in the cross sectional view of the upper supporting member 6 in FIG. 4, is formed on the outer peripheral portion of the boss 63. A moltplene 67 containing grease for sealing a sliding portion of the piston rod 9 is supported to the boss 63 by a pressing washer 68.

The lower supporting member 7 is a disc having a boss 71 through which the supporting shaft 30 extends at a center thereof, and a fixing holes 72 and 73 for respectively fixing the lower ends of the supporting column 51 and the guide pin 5 in such a manner as not to rotate are formed on the outer peripheral portion of the boss 71. The boss 71 is provided with a holding portion 74 on the lower surface thereof all around the periphery, and is slidably supported to the upper surface of the boss 33 of the rotating cylinder 3 through the ball A inserted into the holding portion 74.

The outer cylinder 8 is a parallel tube having an internal diameter slightly larger than the outer diameter of the rotating cylinder 3, and the lower end and the upper end thereof are respectively screwed to the cover 27 and the upper supporting member 6. The outer cylinder 8 is provided with upper and lower two sets of mounting through holes 8a and 8b for mounting an LED chip and a photo sensor at opposing positions with respect to the axis of the outer cylinder 8 on the side surface. Further, the transmitting holes 3a and 3b opposing to each other with respect to the axis of the outer cylinder 8 are provided in the portion of the rotating cylinder in correspondence to these through holes 8a and 8b (refer to FIG. 1).

Figure 6:
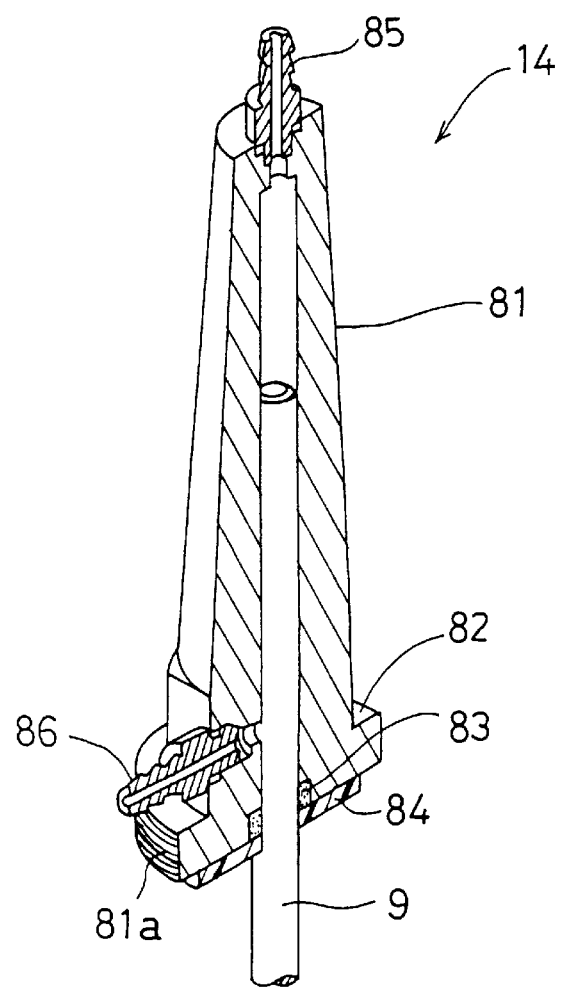
FIG. 6 is a perspective view which partially shows a cross section of a syringe of the syringe pump shown in FIG. 1.

The syringe member 14 comprises, as shown in FIG. 6, the piston rod 9 fixedly attached to the moving element 4 at the lower end thereof and a cylinder 81 slidably holding the piston rod 9 therewithin. A base 82 having a threaded portion 81a engaged with the threaded portion 61a of the upper supporting member 6 on the outer peripheral surface is formed in the base portion of the cylinder 81, and a seal 83 for sealing the sliding portion of the piston rod 9 is supported in the lower end of the base 82 by a seat 84. Further, ports 85 and 86 communicating with each other therewithin are mounted to the upper and lower portions of the cylinder 81.

When the stepping motor 1 is rotated in a normal direction, the rotation of the pinion 21 is transmitted to the rotating cylinder 3 through the reduction gear 2, the lower coupling 28 and the upper coupling 31. When the rotating cylinder 3 is rotated, the force which rotates the moving element 4 engaged with the threaded portion 37 of the rotating cylinder 3 together with the rotating cylinder 3 acts, however, the guide pin 5 and the supporting column 51 supported by the upper supporting member 6 serves as a rotation preventing means for the moving element 4, thereby moving the moving element 4 along the threaded portion 37 of the rotating cylinder 3 in the axial direction. Accordingly, the moving element 4 which is in a waiting state at the lower position in FIG. 2 ascends so as to lift up the piston rod, thereby discharging from the port 85 the liquid which has been introduced through the port 86 and has filled the cylinder 81.

When the stepping motor 1 is rotated in a reverse direction, the moving element 4 (shown in a broken line) in a waiting state at the upper position in FIG. 2 descends so as to press down the piston rod 9 so that the liquid flows into the cylinder 81 in a state of negative pressure from the port 86 so as to fill the inner portion of the cylinder 81.

If the LED chip is disposed in the upper and lower through holes 8a of the outer cylinder 8 and the photo sensor is disposed in the through measuring holes 8b opposing thereto, the upper limit, the lower limit and the middle positions and the moving velocity of the moving element 4 can be measured by detecting the light emitting from the LED chip and passing through the transmitting holes 3a and 3b of the rotating cylinder 3 by means of the photo sensor.

As mentioned above, since the syringe pump 10 can set the lead angle of the screws 37 and 41 to a significantly small value in comparison with the conventional syringe pump, that is, the pump in which the moving element having the piston is moved by the lead screw engaged with the inner peripheral portion thereof, the converting accuracy of the linear converting portion 13 can be improved by decreasing the feeding amount of the moving element 4 per a pulse of the stepping motor 1.

Further, since the guide pin 5 and the supporting column 51 as well as the piston rod 9 can be disposed near the axis of the moving element 4, the pump having a small size and made compact can be formed.

Still further, since the load due to the motion of the piston rod 9 uniformly acts to the threaded portions 37 and 41, the moving element 4 can move to the axial direction in a significantly smooth manner so that the abrasion of the threaded portions 37 and 41 is reduced.

Since the rotating cylinder 3 is supported by the upper supporting member 6 at the upper end portion thereof and is supported by the lower supporting member 7 at the upper surface of the bottom portion thereof, the swing of the rotating cylinder 3 in the radial direction at a time of rotating can be prevented by both the upper and lower of the rotating cylinder 3. Further, the sliding friction between the upper end portion of the rotating cylinder 3 and the upper supporting member 6 can be reduced to the minimum limit by the ball A disposed between the upper end portion and the upper supporting member 6. Accordingly, the expensive bearing such as a ball bearing and the like is not necessary so that the bearing having a simple construction and capable of being formed in an optional portion can be provided.

Since the plurality of guide pins 5 are provided between the upper supporting member 6 and the lower supporting member 7, when the rotating cylinder 3 is going to rotate, the force obtained by that the moving element 4 engaged with the rotating cylinder 3 is going to rotate together with the rotating cylinder 3 can be dispersed into the plurality of guide pins 5. Accordingly, the distortion of the attitude of the guide pin 5 in the radial direction can be prevented.

Further, since the upper supporting member 6 and the lower supporting member 7 can be easily maintained in parallel by the plurality of guide pins 5 and the supporting column 51 and the diameter of the supporting members 6 and 7 can be enlarged, the lead angle of the threaded portions 37 and 41 can be downsize by enlarging the diameter of the moving element 4.

Since the upper and lower supporting members 6 and 7 are fastened to each other in the vertical direction by the column 51, the guide pin 5, the column 51 and the supporting members 6 and 7 improve the rigidity together so as to prevent the distortion of the attitude of the guide pin 5.

Since the syringe pump 10 is constituted by the respective units comprising the rotating portion 12, the linear converting portion 13 and the syringe member 14, assembly, inspection and quality guaranteed can be performed at every units, the assembly can be easily performed by binding by screws, and quality control can be easily performed.

Further, since the motion information concerning the piston rod 9 can be obtained by mounting the above luminous means and the light receiving means to the outer cylinder 8 supporting the rotating cylinder 3 so that a simple optical measurement can be performed without newly providing an excess space.

The present invention has been explained so far by the example having a syringe composed of a set of a piston rod and a cylinder. However, in the present invention, it is also possible to provide a plurality of syringes, i.e., plural sets of pistons rod and cylinders. In this case, it is preferable that the pistons are positioned in good balance on a surface of the moving element which is perpendicular to the axis so that the surface is not inclined when the moving element received a load from the pistons.

Figure 7:
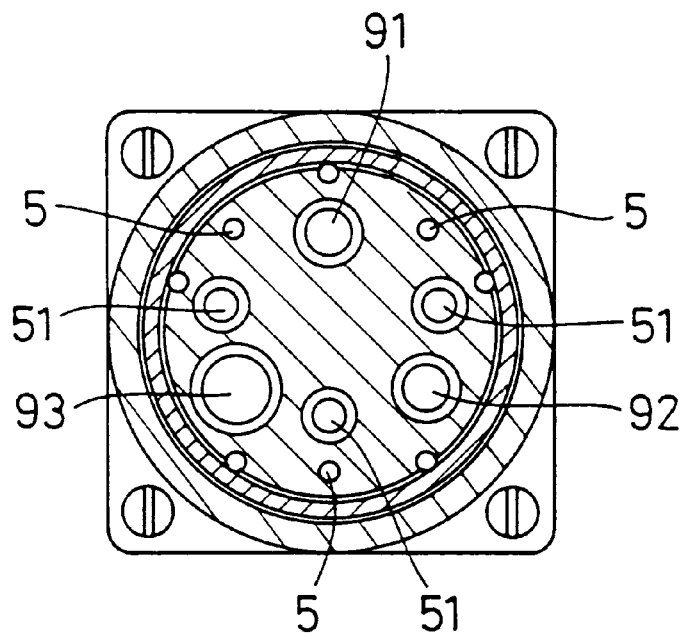
FIG. 7 shows a syringe pump in accordance with an alternative embodiment of the present invention corresponding to FIG. 7.

Referring to FIG. 7, an example provided with three syringes is described. FIG. 7 corresponds to FIG. 5. Here three piston rods 91, 92 and 93 having different outer diameters are placed at regular spaces on the moving element 4 equidistantly from the center of the moving element 4. Three support columns 51 and three guide pins 5 are aslo paced on the moving element 4 equidistantly from the center of the moving elements 4, as shown in FIG. 5. Three cylinders (not shown) are provided corresponding to the respective piston rods 91, 92 and 93. Each of these three cylinders is formed in one piece. By thus placing the piston rods 91, 92 and 93 in good balance on the moving element 4, a load caused by operation of the piston rods 91, 92 and 93 is allowed to act on a threaded portion 41 uniformly. Therefore, the moving element 4 moves smoothly and the threaded portion 41 is abraded less.

Figure 8:
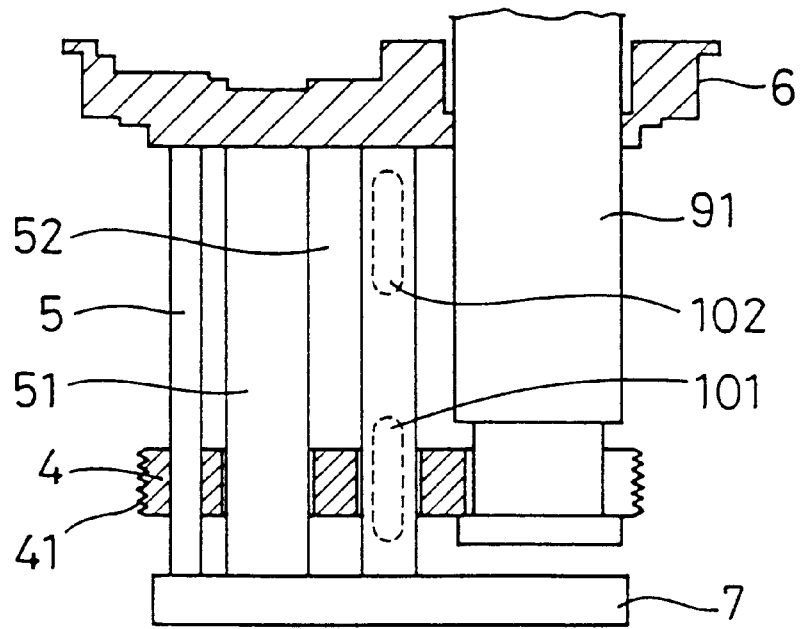
FIG. 8 is a cross sectional view which shows a part of syringe pump in accordance with a further alternative embodiment of the present invention corresponding to FIG. 2.

In this example, there is room in a central part of the linear converting portion. For utilizing the room efficiently, a supporting column may be provided between the upper and lower supporting members 6 and 7 and a sensor such as a lead switch may be mounted on the supporting column to detect the position of the moving elements. FIG. 8 shows an example of such embodiment. Referring to FIG. 8, fixed electrodes 101 and 102 are mounted on a supporting column 52 at certain heights along the direction of the axis so as to detect the postition of the moving element 4 which is constructed to be a moving electrode.

In another example, the piston rods 91, 92 and 93 may be mounted on the moving element 4 with different gaps between the piston rods and the moving element to vary the timing of the piston rods 91, 92 and 93 starting to move. Thus a plurality of pistons can be operated at desired time lags by one driving source so as to provide large variety for the control of fluid systems.

The invention enables the downsizing of syringe pumps because the driver linear converting portion and syringe body can be coaxially disposed.

In accordance with the syringe pump of the present invention, since it is structured such that when the rotating cylinder is rotated, the moving element engaged with the female screw formed on the inner peripheral surface of the rotating cylinder move in the axial direction, the lead angle of the threaded portions can be set to a significantly small value in comparison with the conventional syringe pump using the lead screw such as in the above conventional embodiment so that the moving accuracy of the piston can be improved by decreasing the feeding amount of the moving element with respect to the rotating amount of the rotating shaft.

Since the upper supporting member pivotally supports the rotating cylinder at the upper end portion of the rotating cylinder in such a manner as to rotate, the swing in a radial direction and an axial direction in the upper portion of the rotating cylinder can be prevented. Further, since the lower supporting member supports the rotating cylinder at the upper surface portion of the bottom portion of the rotating cylinder in such a manner as to rotate, the swing in the lower portion of the rotating cylinder can be prevented. Since the guide pin is supported by the upper and lower supporting members at both ends thereof, the guide axis effectively operates as the rotation preventing mechanism for the moving element. Further, if the upper and lower supporting members are vertically fastened to each other by the guide pin, the guide pin and the supporting members integrally improve the rigidity, the distortion of the attitude of the guide pin can be prevented and the upper and lower supporting members in a cooperating manner support an upper and lower two portions of the rotating cylinder so that the total swing of the rotating cylinder in the radial direction and the axial direction can be effectively prevented.

If the plurality of guide pins are provided between the upper supporting member and the lower supporting member, when the rotating cylinder is going to rotate, the force obtained by that the moving element engaged with the rotating cylinder is going to rotate together with the rotating cylinder can be dispersed into the plurality of guide pins. Accordingly, the distortion of the attitude of the guide pin in the radial direction can be prevented. Further, the upper supporting member and the lower supporting member can be easily maintained in parallel.

Accordingly, the diameter of the supporting members can be enlarged, the lead angle of the threaded portions can be downsize and the moving element can be moved with much improved accuracy.

Further, since the guide pin as well as the piston can be disposed near the axis of the moving element, the pump having a small size and made compact can be formed. Still further, since the load due to the motion of the piston uniformly acts to the threaded portions, the moving element can move to the axial direction in a significantly smooth manner so that the abrasion of the threaded portions is reduced.

As the syringe piston comprises a plurality of syringe pistons dispersedly provided on the moving element and the syringe cylinder comprises a plurality of syringe cylinders corresponding to the syringe pistons, it is possible to operate a plurality of fluid systems with one driving source and to reduce the site of the whole apparatus.

By placing the syringe pistons in good balance around the center of the moving element, for example, by dispersing a plurality of syringe pistons symmetrically around the center of the moving element, the load caused by operation of the pistons acts uniformly on a threaded portion. Therefore, the moving element moves smoothly and the threaded portion is abraded less.

In accordance with the present invention, a compact syringe pump having a high quantitative accuracy and a high durability can be provided.

What is claimed is:

1. A syringe pump comprising:

a driving means having a rotating shaft;

a rotating cylinder having a bottom, a connecting portion capable of connecting with the driving means at a lower surface of the bottom and a threaded portion formed in an inner peripheral portion;

a moving element having in an outer peripheral portion; a threaded portion to engage with the threaded portion of the rotating cylinder;

a guide means for introducing the moving element in an axial direction of the rotating cylinder by restricting the rotation of the moving element when the rotating cylinder rotates through the connecting portion;

a syringe piston disposed on the moving element; and a syringe cylinder within which the syringe piston moves, wherein the guide means comprises a guide pin extending through the moving element in the axial direction of the rotating cylinder and a pair of upper supporting member and lower supporting member for supporting both ends of the guide pin so that the guide pin becomes in parallel to the axial direction of the rotating cylinder, and the supporting members are structured such that the upper supporting member rotatably supports the rotating cylinder at an upper end portion of the rotating cylinder and the lower supporting member rotatably supports the rotating cylinder at an upper surface of the bottom of the rotating cylinder.

2. A syringe pump according to claim 1, wherein the guide pin comprises a plurality of guide pins provided between the upper supporting member and the lower supporting member.

3. A syringe pump according to claim 1, wherein the syringe piston comprises a plurality of syringe pistons dispersedly disposed on the moving element and the syringe cylinder comprises a plurality of syringe cylinders provided corresponding to the syringe pistons.

4. A syringe pump according to claim 3, wherein a gap for generating an idle time before the syringe piston starts to move is provided between the moving element and each of the syringe pistons.

5. A syringe pump according to claim 3, wherein the timing of the syringe pistons starting to move is varied.

\* \* \* \* \*